United States Patent
Maier et al.

(10) Patent No.: US 7,776,792 B2
(45) Date of Patent: Aug. 17, 2010

(54) AGROCHEMICAL FORMULATIONS

(75) Inventors: Thomas Maier, Hofheim (DE); Gerhard Schnabel, Elsenfeld (DE); Detlev Haase, Frankfurt (DE); Jochen Würtz, Bad Kreuznach (DE)

(73) Assignee: Bayer CropScience AG (DE)

( * ) Notice: Subject to any disclaimer, the term of this patent is extended or adjusted under 35 U.S.C. 154(b) by 936 days.

(21) Appl. No.: 10/468,190

(22) PCT Filed: Jan. 19, 2002

(86) PCT No.: PCT/EP02/00500

§ 371 (c)(1), (2), (4) Date: Dec. 18, 2003

(87) PCT Pub. No.: WO02/067676

PCT Pub. Date: Sep. 6, 2002

(65) Prior Publication Data

US 2004/0097378 A1  May 20, 2004

(30) Foreign Application Priority Data

Feb. 22, 2001 (DE) ................ 101 08 472

(51) Int. Cl.
*A01N 47/36* (2006.01)
*A01N 25/04* (2006.01)
(52) U.S. Cl. ..................... 504/363; 504/211
(58) Field of Classification Search .................. 504/363
See application file for complete search history.

(56) References Cited

U.S. PATENT DOCUMENTS

| 4,626,274 A | 12/1986 | Hausmann et al. |
| 5,092,918 A | 3/1992 | Kuchikata |
| 5,731,264 A * | 3/1998 | Narayanan et al. .......... 504/363 |
| 6,087,305 A | 7/2000 | Kober et al. |
| 6,569,805 B1 * | 5/2003 | Krahmer et al. ............. 504/103 |
| 2002/0016263 A1 | 2/2002 | Wurtz et al. |
| 2002/0091066 A1 | 7/2002 | Wurtz et al. |

FOREIGN PATENT DOCUMENTS

| EP | 0113857 | 7/1984 |
| EP | 1023833 | 8/2000 |
| EP | 1023833 A2 * | 8/2000 |
| GB | 2309904 | 8/1997 |
| WO | WO-98/16102 | 4/1998 |
| WO | WO-01/82693 | 11/2001 |
| WO | WO-01/97615 | 12/2001 |

OTHER PUBLICATIONS

Derwent Abstract of AN-1998-433651, XP-002202665 & JP 10-182302 A (Takeda Chem Ind Ltd) (Jul. 7, 1998).
Suzuki Shoji, "Stabilized Solid Agrochemical Formulation," Patent Abstracts of Japan 1999 (No. 03): Abs. of JP 10 324606 A, (Nissan Chem Ind Ltd) (Dec. 8, 1998).
Derwent Abstract of AN-1996-368033, XP-002202666 & JP 03-237077 B (Hokko Chem Ind Co Ltd) (Dec. 10, 2001).

* cited by examiner

*Primary Examiner*—Jake M. Vu
(74) *Attorney, Agent, or Firm*—Connolly Bove Lodge & Hutz LLP

(57) ABSTRACT

The invention relates to liquid formulations (preparations) that contain a) one or more alkyl esters of polycarboxylic acids, and b) one or more agrochemical substances from the group of ALS inhibitors.

9 Claims, No Drawings

AGROCHEMICAL FORMULATIONS

The present invention relates to the field of agrochemical formulations in particular liquid formulations of agrochemically active compounds such as acetolactate synthase inhibitors (ALS inhibitors), for example sulfonylureas and salts thereof.

ALS inhibitors are substances which are used in agrochemistry mainly as herbicides. Owing to their low application rate and their generally broad activity spectra, ALS inhibitors are used in all crops of economical importance.

In general, agrochemically active compounds are not employed as pure substances but, depending on the area of use and the desired physical properties of the use form, in combination with certain auxiliaries, i.e. they are "formulated". In principle, active compounds can be formulated in various ways, depending on the prevailing biological and/or physicochemical parameters. The following are examples of general possibilities for formulations: wettable powders (WP), oil-in-water or water-in-oil emulsions (EW and EO, respectively), suspensions (SC), suspoemulsions (SE), emulsifiable concentrates (EC), aqueous solutions (SL) or else granules for soil application or for broadcasting, or water-dispersible granules (WG). The formulation types mentioned are known in principle and are described, for example, in: Winnacker-Küchler, "Chemische Technologie" [Chemical Technology], volume 7, C. Hauser-Verlag, Munich, 4th edition, 1986; van Valkenburg, "Pesticide Formulations", Marcel-Dekker N.Y., 1973; K. Martens, "Spray Drying Handbook", 3rd ed., 1979, G. Goodwin Ltd. London.

If the agrochemically active compounds to be formulated are compounds which generally tend to degrade chemically in the dissolved state or in liquid media, preference is usually given to solid formulations such as wettable powders or granules. As described in U.S. Pat. No. 4,599,412 and U.S. Pat. No. 5,731,264, this is the case, for example, for herbicidally active compounds from the group of the ALS inhibitors, such as metsulfuronmethyl, nico- or rimsulfuron, primisulfuronmethyl, tria-, pro-, amido- or ethoxysulfuron. Accordingly, powder formulations or granules of these herbicides—as, for example, in WO9910857, WO9809516, WO9508265, U.S. Pat. No. 5,441,923, WO9423573, JP05017305, JP04297404, JP04297403 or JP04066509—are already known.

Frequently, when such powder formulations or granules are diluted with water (to prepare the spray liquor), the undissolved fractions in the concentrate cannot be dissolved completely, i.e. the spray liquor is a suspension of the concentrate. However, it is always advantageous if spray liquors are as finely divided as possible, since this reduces the risk of the spray nozzles being blocked and thus quite generally the expenditure for cleaning. Moreover, powder and granule formulations can only be prepared with a relatively high input of energy and technically complicated stirrers, i.e. there are considerable disadvantages even during their preparation.

Liquid suspensions of herbicides of the kind described above in the form of suspension concentrates are already known (FR2576181, EP0205348, EP0237292 or EP0246984). However, in the case of suspensions, too, the active compounds are not dissolved, so that during application of the spray liquor similar problems are encountered as in the case of powder formulations or granules. Moreover, suspension concentrates (SC) and suspoemulsions (SE) are thermodynamically unstable formulations having limited physical storage stability.

Surfactant-free aqueous solutions of sulfonylureas are described in U.S. Pat. Nos. 4,683,000, 4,671,817 and EP0245058, water-free emulsifiable concentrates are described in the publications DE3422824, U.S. Pat. No. 4,632,693, WO9608148 and U.S. Pat. No. 5,597,778. None of these publications give any hints on how to increase the storage stability of the formulations.

Accordingly, it was an object of the present invention to provide an agrochemical formulation which is stable to degradation and which has favorable performance properties.

Surprisingly, it has now been found that this object is achieved by certain liquid active compound formulations comprising specific polycarboxylic acid esters and, as agrochemically active compounds, ALS inhibitors such as, for example, sulfonylureas and/or salts thereof.

Accordingly, the present invention provides a liquid formulation (preparation), comprising a) one or more compounds from the group of the alkyl esters of polycarboxylic acids, preferably one or more compounds from the group of the $C_1$-$C_{20}$-alkyl esters of polycarboxylic acids, and b) one or more agrochemically active compounds from the group of the ALS inhibitors, in particular one or more sulfonylureas and/or salts thereof, for example salts with organic cations based on nitrogen, sulfur or phosphorus and/or inorganic cations such as metal cations.

The liquid formulations of the present invention are preferably herbicidal formulations, for example in the form of emulsion concentrates. The formulations preferably comprise at least one of the active compounds from the group of the ALS inhibitors in dissolved form, the polycarboxylic acid alkyl esters a) serving as solvent. Preference is furthermore given to formulations which comprise only one polycarboxylic acid alkyl ester a).

If appropriate, the liquid formulations of the present invention may, in addition to components a) and b), also comprise one or more auxiliaries and additives as further components, for example:

(c) surfactants and/or non-surfactant polymers,
(d) organic solvents different from component a),
(e) agrochemicals which are different from ALS inhibitors, such as herbicides, insecticides, fungicides, safeners, growth regulators or fertilizers,
(f) customary formulation auxiliaries, such as antifoams, evaporation inhibitors, odorants, colorants, antifreeze agents or preservatives, stabilizers, dessicants or thickeners,
(g) tank mix components, and/or
(h) additional water.

The polycarboxylic acid alkyl esters which are present in the formulations according to the invention as component a) can act as solvent and are, for example, alkyl esters of low-molecular-weight dicarboxylic acids, tricarboxylic acids, tetracarboxylic acids or else carboxylic acids of higher functionality, preferably having 2-20 carbon atoms. Also suitable are polymeric polycarboxylic acids, preferably having molecular weights of up to 2 000 g/mol. Examples of polycarboxylic acids are oxalic, malonic, succinic, glutaric, adipic, pimelic, sebacic, azelaic, suberic, maleic, phthalic, terephthalic, mellitic, trimellitic, polymaleic, polyacrylic and polymethacrylic acid and also co- or terpolymers comprising maleic, acrylic and/or methacrylic acid units.

Suitable alcohol components of the polycarboxylic acid alkyl esters a) are, for example, alkyl alcohols, preferably monofunctional alkyl alcohols having 1-20 carbon atoms. Examples for such alkyl alcohols are methyl alcohol, ethyl alcohol, n-propyl alcohol, iso-propyl alcohol, n-butyl alcohol, sec-butyl alcohol, iso-butyl alcohol and tert-butyl alcohol.

The polycarboxylic acid alkyl esters a) preferably have the formula (I) below $$R^\gamma\text{—O—OC—}(CR^\alpha R^\beta)_x\text{—CO—O—}R^\delta \quad (I)$$

in which $R^\alpha$ and $R^\beta$ are identical or different and are H, an unsubstituted or substituted $C_1$-$C_{20}$-hydrocarbon radical, such as $C_1$-$C_{10}$-alkyl, or a group $(CR'R'')_y$—CO—OR''', in which R' and R'' are identical or different and are H or an unsubstituted or substituted $C_1$-$C_{20}$-hydrocarbon radical, such as $C_1$-$C_{10}$-alkyl, y is an integer from 0 to 10 and R''' is an unsubstituted or substituted $C_1$-$C_{20}$-hydrocarbon radical, such as $C_1$-$C_{10}$ alkyl, $R^\gamma$ and $R^\delta$ are identical or different and are an unsubstituted or substituted $C_1$-$C_{20}$-hydrocarbon radical, such as $C_1$-$C_{10}$ alkyl, and x is an integer from 0 to 20.

Particularly preferred polycarboxylic acid alkyl esters a) are diesters of the formula (Ia) below $$R^\gamma\text{—O—OC—}(CH_2)_x\text{—CO—O—}R^\delta \quad (Ia)$$

in which x is an integer from 0 to 20 and $R^\gamma$ and $R^\delta$ independently of one another are identical or different $C_1$-$C_6$-alkyl radicals.

Examples of polycarboxylic acid alkyl esters a) are oxalic acid esters, such as dimethyl oxalate, diethyl oxalate, di-n-propyl oxalate, diisopropyl oxalate and methyl ethyl oxalate, malonic acid esters, such as dimethyl malonate, diethyl malonate, di-n-propyl malonate, diisopropyl malonate and methyl ethyl malonate, succinic acid esters, such as dimethyl succinate, diethyl succinate, di-n-propyl succinate, diisopropyl succinate and methyl ethyl succinate, glutaric acid esters, such as dimethyl glutarate, diethyl glutarate, di-n-propyl glutarate, diisopropyl glutarate and methyl ethyl glutarate, and adipic acid esters, such as dimethyl adipate, diethyl adipate, di-n-propyl adipate, diisopropyl adipate and methyl ethyl adipate. Preference is given to adipic acid esters, in particular to dimethyl adipate.

The polycarboxylic acid alkyl esters a) can be obtained, for example, by reacting the free carboxylic acids with the alcohols, it being possible to obtain the esters for example by reacting "activated" polycarboxylic acids, such as polycarboxylic anhydrides or polycarbonyl (poly)chlorides, with the alcohols following known esterification methods.

The active compounds from the group of the ALS inhibitors present in the formulations according to the invention as component b) are in particular imidazolinones, pyrimidinyloxypyridinecarboxylic acid derivatives, pyrimidinyloxybenzoic acid derivatives, triazolopyrimidinesulfonamide derivatives or sulfonamides, preferably from the group of the sulfonylureas, particularly preferably those of the formula (II) and/or salts thereof:

$$R^a\text{—SO}_2\text{—NR}^b\text{—CO—}(NR^c)_x\text{—}R^d \quad (II)$$

in which $R^a$ is a hydrocarbon radical, preferably an aryl radical such as phenyl, which is unsubstituted or substituted, or a heterocyclic radical, preferably a heteroaryl radical such as pyridyl, which is unsubstituted or substituted, where the radicals including substituents have 1-30 carbon atoms, preferably 1-20 carbon atoms, or $R^a$ is an electron-withdrawing group, such as a sulfonamide radical, $R^b$ is a hydrogen atom or a hydrocarbon radical, which is unsubstituted or substituted and, including substituents, has 1-10 carbon atoms, for example unsubstituted or substituted $C_1$-$C_6$-alkyl, preferably a hydrogen atom or methyl, $R^c$ is a hydrogen atom or a hydrocarbon radical, which is unsubstituted or substituted and, including substituents, has 1-10 carbon atoms, for example unsubstituted or substituted $C_1$-$C_6$-alkyl, preferably a hydrogen atom or methyl, x is zero or 1, and $R^d$ is a heterocyclyl radical.

For the purpose of this description, a hydrocarbon radical is a straight-chain, branched or cyclic, saturated or unsaturated aliphatic or aromatic hydrocarbon radical, for example alkyl, alkenyl, alkynyl, cycloalkyl, cycloalkenyl or aryl; aryl is a mono-, bi- or polycyclic aromatic system, for example phenyl, naphthyl, tetrahydronaphthyl, indenyl, indanyl, pentalenyl, fluorenyl and the like, preferably phenyl. Unless stated otherwise, a hydrocarbon radical has preferably 1 to 40 carbon atoms, more preferably 1 to 30 carbon atoms; particularly preferably, a hydrocarbon radical is alkyl, alkenyl or alkynyl having up to 12 carbon atoms or cycloalkyl having 3, 4, 5, 6 or 7 ring atoms or phenyl. A hydrocarbonoxy radical is a hydrocarbon radical which is defined as above and attached via an oxygen atom.

For the purpose of this description, a heterocyclic radical or ring (heterocyclyl) can be saturated, unsaturated or heteroaromatic and be unsubstituted or substituted; it preferably contains one or more heteroatoms in the ring, preferably from the group consisting of N, O and S; it is preferably an aliphatic heterocyclyl radical having 3 to 7 ring atoms or a heteroaromatic radical having 5 or 6 ring atoms and contains 1, 2 or 3 heteroatoms. The heterocyclic radical can, for example, be a heteroaromatic radical or ring (heteroaryl), such as, for example, a mono-, bi- or polycyclic aromatic system in which at least one ring contains one or more heteroatoms, for example pyridyl, pyrimidinyl, pyridazinyl, pyrazinyl, triazinyl, thienyl, thiazolyl, oxazolyl, furyl, pyrrolyl, pyrazolyl and imidazolyl, or is a partially or fully hydrogenated radical, such as oxiranyl, oxetanyl, pyrrolidyl, piperidyl, piperazinyl, dioxolanyl, morpholinyl, tetrahydrofuryl. Suitable substituents for a substituted heterocyclic radical are the substituents mentioned further below, and additionally also oxo. The oxo group may also be present at the hetero ring atoms, which may exist in different oxidation states, for example N and S.

For the purpose of this description, substituted radicals, such as substituted hydrocarbon radicals, for example substituted alkyl, alkenyl, alkynyl or aryl, such as phenyl or benzyl or substituted heterocyclyl, are, for example, substituted radicals which are derived from an unsubstituted parent compound, where the substituents are, for example, one or more, preferably 1, 2 or 3, radicals from the group consisting of halogen (fluorine, chlorine, bromine, iodine), alkoxy, haloalkoxy, alkylthio, hydroxyl, amino, nitro, carboxyl, cyano, azido, alkoxy-carbonyl, alkylcarbonyl, formyl, carbamoyl, mono- and dialkylaminocarbonyl, substituted amino, such as acylamino, mono- and dialkylamino, and alkylsulfinyl, haloalkylsulfinyl, alkylsulfonyl, haloalkylsulfonyl and, in the case of cyclic radicals, also alkyl and haloalkyl, and unsaturated aliphatic radicals which correspond to the saturated hydrocarbon-containing radicals mentioned, such as alkenyl, alkynyl, alkenyloxy, alkynyloxy, etc. Among the radicals with carbon atoms, preference is given to those having 1 to 4 carbon atoms, in particular 1 or 2 carbon atoms. Preference is generally given to substituents from the group consisting of halogen, for example fluorine and chlorine, $(C_1$-$C_4)$alkyl, preferably methyl or ethyl, $(C_1$-$C_4)$haloalkyl, preferably trifluoromethyl, $(C_1-C_4)$alkoxy, preferably methoxy or ethoxy, $(C_1-C_4)$haloalkoxy, nitro and cyano.

For the purpose of this description, the aliphatic radicals, such as alkyl, alkoxy, haloalkyl, alkylamino and alkylthio radicals, and the corresponding unsaturated and/or substituted radicals, can in each case be straight-chain or branched in the carbon skeleton and, for carbon numbers of 3 or more, also be cyclic. Among these radicals, preference is given, unless specifically indicated otherwise, to lower carbon skeletons, for example those having 1 to 6 carbon atoms or, in the case of unsaturated groups, having 2 to 6 carbon atoms.

Alkyl radicals, also in composite meanings such as alkoxy, haloalkyl, etc., are, for example, methyl, ethyl, n-, iso- or cyclopropyl, n-, iso-, tert-, 2- or cyclobutyl, pentyls, hexyls, such as n-hexyl, iso-hexyl and 1,3-dimethylbutyl, heptyls, such as n-heptyl, 1-methylhexyl and 1,4-dimethylpentyl; alkenyl and alkynyl radicals have the meanings of the possible unsaturated radicals corresponding to the alkyl radicals; alkenyl is, for example, allyl, 1-methyl-prop-2-en-1-yl, 2-methyl-prop-2-en-1-yl, but-2-en-1-yl, but-3-en-1-yl, 1-methylbut-3-en-1-yl and 1-methyl-but-2-en-1-yl; alkynyl is, for example, propargyl, but-2-yn-1-yl, but-3-yn-1-yl, 1-methylbut-3-yn-1-yl.

Halogen is, for example, fluorine, chlorine, bromine or iodine. Haloalkyl, -alkenyl and -alkynyl is alkyl alkenyl and alkynyl, respectively, which is partially or fully substituted by halogen, preferably by fluorine, chlorine and/or bromine, in particular by fluorine or chlorine, for example $CF_3$, $CHF_2$, $CH_2F$, $CF_3CF_2$, $CH_2FCHCl$, $CCl_3$, $CHCl_2$, $CH_2CH_2Cl$; haloalkoxy is, for example, $OCF_3$, $OCHF_2$, $OCH_2F$, $CF_3CF_2O$, $OCH_2CF_3$ and $OCH_2CH_2Cl$; this applies correspondingly to haloalkenyl and other halogen-substituted radicals.

For the purpose of the present invention, the active compounds from the group of the ALS inhibitors which are present as component b) in the liquid formulations according to the invention, such as sulfonylureas, include, in addition to the neutral compounds, in each case also their agriculturally suitable salts with inorganic and/or organic counterions.

The sulfonylureas, for example those of the formula (II), can, for example, form salts in which the hydrogen of the —$SO_2$—NH-group is replaced by an agriculturally suitable cation. These salts are, for example, metal salts, in particular alkali metal salts or alkaline earth metal salts, in particular sodium and potassium salts, or else ammonium, sulfonium or phosphonium salts. Salt formation may also take place by addition of an acid to basic groups, such as, for example, amino and alkylamino. Acids suitable for this purpose are strong inorganic and organic acids, for example HCl, HBr, $H_2SO_4$ or $HNO_3$.

Suitable salts having inorganic counterions are, for example, salts having $NH_4^\oplus$, $SH_3^\oplus$ or $PH_4^\oplus$ counterions, or metal salts having, for example, alkali metal or alkaline earth metal counterions such as $Na^\oplus$, $K^\oplus$, $½Mg^{2\oplus}$ or $½Ca^{2\oplus}$. Suitable salts with organic counterions are, for example, organic ammonium, sulfonium and phosphonium salts. Preference is given to organic counterions of the formula $[NR^8R^9R^{10}R^{11}]^+$, $[SR^2R^{13}R^{14}]^+$ or $[PR^{15}R^{16}R^{17}R^{18}]^+$, or to a quaternary pyridinium ion $[Py—R^{19}]^+$, where $R^8$ to $R^{19}$ independently of one another are identical or different and are H or unsubstituted or substituted hydrocarbon radicals, such as unsubstituted or substituted $(C_1-C_{30})$-alkyl, unsubstituted or substituted $(C_1-C_{10})$-alkylaryl, unsubstituted or substituted $(C_3-C_{30})$-(oligo)alkenyl, unsubstituted or substituted $(C_3-C_{10})$-(oligo)alkenylaryl, unsubstituted or substituted $(C_3-C_{30})$-(oligo)alkynyl, unsubstituted or substituted $(C_3-C_{10})$-(oligo)alkynyl, aryl or unsubstituted or substituted aryl, or an unsubstituted or substituted heterocyclyl radical, in particular heteroaryl radical, such as unsubstituted or substituted $(C_1-C_{10})$-alkyl-heteroaryl, unsubstituted or substituted $(C_3-C_{10})$-(oligo)alkenyl-heteroaryl, unsubstituted or substituted $(C_3-C_{10})$-(oligo)alkynyl-heteroaryl or unsubstituted or substituted heteroaryl, or two radicals $R^8/R^9$, $R^{10}/R^{11}$, $R^{12}/R^{13}$, $R^{15}/R^{16}$ or $R^{17}/R^{18}$ together may form an unsubstituted or substituted ring, where at least one of the radicals $R^8$—$R^{11}$, at least one of the radicals $R^{12}$-$R^{14}$ and at least one of the radicals $R^{15}$-$R^{18}$ is different from H.

Preferred ALS inhibitors originate from the group of the sulfonylureas, for example pyrimidine- or triazinylaminocarbonyl[benzene-, pyridine-, pyrazole-, thiophene- and (alkylsulfonyl)alkylamino]sulfamides. Preferred substituents on the pyrimidine ring or triazine ring are alkoxy, alkyl, haloalkoxy, haloalkyl, halogen or dimethylamino, where all substituents can be combined independently of one another. Preferred substituents in the benzene, pyridine, pyrazole, thiophene or (alkylsulfonyl)alkylamino moiety are alkyl, alkoxy, halogen, amino, alkylamino, dialkylamino, acylamino, acylaminomethyl, nitro, alkoxycarbonyl, aminocarbonyl, alkylaminocarbonyl, dialkylaminocarbonyl, alkoxyaminocarbonyl, haloalkoxy, haloalkyl, alkylcarbonyl, alkoxyalkyl, (alkanesulfonyl)alkylamino. Such suitable sulfonylureas are, for example, b1) phenyl- and benzylsulfonylureas and related compounds, for example
1-(2-chlorophenylsulfonyl)-3-(4-methoxy-6-methyl-1,3,5-triazin-2-yl)urea (chlorsulfuron),
1-(2-ethoxycarbonylphenylsulfonyl)-3-(4-chloro-6-methoxypyrimidin-2-yl)urea (chlorimuron-ethyl),
1-(2-methoxyphenylsulfonyl)-3-(4-methoxy-6-methyl-1,3,5-triazin-2-yl)urea (metsulfuron-methyl),
1-(2-chloroethoxyphenylsulfonyl)-3-(4-methoxy-6-methyl-1,3,5-triazin-2-yl)urea (triasulfuron),
1-(2-methoxycarbonylphenylsulfonyl)-3-(4,6-dimethylpyrimidin-2-yl)urea (sulfumeturon-methyl),
1-(2-methoxycarbonylphenylsulfonyl)-3-(4-methoxy-6-methyl-1,3,5-triazin-2-yl)-3-methylurea (tribenuron-methyl),
1-(2-methoxycarbonylbenzylsulfonyl)-3-(4,6-dimethoxypyrimidin-2-yl)urea (bensulfuron-methyl),
1-(2-methoxycarbonylphenylsulfonyl)-3-(4,6-bis(difluoromethoxy)pyrimidin-2-yl)urea (primisulfuron-methyl),
3-(4-ethyl-6-methoxy-1,3,5-triazin-2-yl)-1-(2,3-dihydro-1,1-dioxo-2-methylbenzo-[b]thiophene-7-sulfonyl)urea (EP-A 0 796 83),
3-(4-ethoxy-6-ethyl-1,3,5-triazin-2-yl)-1-(2,3-dihydro-1,1-dioxo-2-methylbenzo[b]-thiophene-7-sulfonyl)urea (EP-A 0 079 683),
3-(4-methoxy-6-methyl-1,3,5-triazin-2-yl)-1-(2-methoxycarbonyl-5-iodophenyl-sulfonyl)urea (iodosulfuronmethyl and its salts such as the sodium salt, WO 92/13845),
DPX-66037, triflusulfuron-methyl (see Brighton Crop Prot. Conf.—Weeds—1995, p. 853),
CGA-277476 (see Brighton Crop Prot. Conf.—Weeds—1995, p. 79),
methyl 2-[3-(4,6-dimethoxypyrimidin-2-yl)ureidosulfonyl]-4-methanesulfonamido-methylbenzoate (mesosulfuronmethyl and its salts such as the sodium salt, WO 95/10507),
N,N-dimethyl-2-[3-(4,6-dimethoxypyrimidin-2-yl)ureidosulfonyl]-4-formylamino-benzamide (foramsulfuron and its salts such as the sodium salt, WO 95/01344);

b2) thienylsulfonylureas, for example
1-(2-methoxycarbonylthiophen-3-yl)-3-(4-methoxy-6-methyl-1,3,5-triazin-2-yl)urea (thifensulfuron-methyl);

b3) pyrazolylsulfonylureas, for example 1-(4-ethoxycarbonyl-1-methylpyrazol-5-ylsulfonyl)-3-(4,6-dimethoxypyrimidin-2-yl)urea (pyrazosulfuron-methyl);

methyl 3-chloro-5-(4,6-dimethoxypyrimidin-2-ylcarbamoylsulfamoyl)-1-methyl-pyrazole-4-carboxylate (EP-A 0 282 613);

methyl 5-(4,6-dimethylpyrimidin-2-ylcarbamoylsulfamoyl)-1-(2-pyridyl)-pyrazole-4-carboxylate (NC-330, see Brighton Crop Prot. Conference "Weeds" 1991, Vol. 1, p. 45ff.), DPX-A8947, azimsulfuron, (see Brighton Crop Prot. Conf. "Weeds" 1995, p. 65);

b4) sulfondiamide derivatives, for example 3-(4,6-dimethoxypyrimidin-2-yl)-1-(N-methyl-N-methylsulfonylaminosulfonyl)urea (amidosulfuron) and its structural analogs (EP-A 0 131 258 and Z. Pfl. Krankh. Pfl. Schutz, special edition XII, 489-497 (1990));

b5) pyridylsulfonylureas, for example 1-(3-N,N-dimethylaminocarbonylpyridin-2-ylsulfonyl)-3-(4,6-dimethoxypyrimidin-2-yl)urea (nicosulfuron), 1-(3-ethylsulfonylpyridin-2-ylsulfonyl)-3-(4,6-dimethoxypyrimidin-2-yl)urea (rimsulfuron), methyl 2-[3-(4,6-dimethoxypyrimidin-2-yl)ureidosulfonyl]-6-trifluoromethyl-3-pyridine-carboxylate, sodium salt (DPX-KE 459, flupyrsulfuron, see Brighton Crop Prot. Conf. Weeds, 1995, p. 49), pyridylsulfonylureas, as described, for example, in DE-A 40 00 503 and DE-A 40 30 577, preferably those of the formula

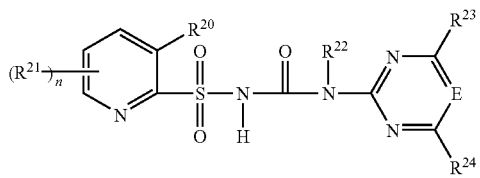

in which

E is CH or N, preferably CH, $R^{20}$ is iodine or $NR^{25}R^{26}$, $R^{21}$ is hydrogen, halogen, cyano, $(C_1-C_3)$-alkyl, $(C_1-C_3)$-alkoxy, $(C_1-C_3)$-haloalkyl, $(C_1-C_3)$-haloalkoxy, $(C_1-C_3)$-alkylthio, $(C_1-C_3)$-alkoxy-$(C_1-C_3)$-alkyl, $(C_1-C_3)$-alkoxycarbonyl, mono- or di-$((C_1-C_3)$-alkyl)amino, $(C_1-C_3)$-alkylsulfinyl or -sulfonyl, $SO_2$—$NR^xR^y$ or $CO$—$NR^xR^y$, in particular hydrogen, $R^x$, $R^y$ independently of one another are hydrogen, $(C_1-C_3)$-alkyl, $(C_1-C_3)$-alkenyl, $(C_1-C_3)$-alkynyl or together are —$(CH_2)_4$—, —$(CH_2)_5$— or —$(CH_2)_2$—O—$(CH_2)_2$—, n is 0, 1, 2 or 3, preferably 0 or 1, $R^{22}$ is hydrogen or $CH_3$, $R^{23}$ is halogen, $(C_1-C_2)$-alkyl, $(C_1-C_2)$-alkoxy, $(C_1-C_2)$-haloalkyl, in particular $CF_3$, $(C_1-C_2)$-haloalkoxy, preferably $OCHF_2$ or $OCH_2CF_3$, $R^{24}$ is $(C_1-C_2)$-alkyl, $(C_1-C_2)$-haloalkoxy, preferably $OCHF_2$, or $(C_1-C_2)$-alkoxy, $R^{25}$ is $(C_1-C_4)$-alkyl, $R^{26}$ is $(C_1-C_4)$-alkylsulfonyl or $R^{25}$ and $R^{26}$ together are a chain of the formula —$(CH_2)_3$SO$_2$— or —$(CH_2)_4SO_2$—, for example 3-(4,6-dimethoxypyrimidin-2-yl)-1-(3-N-methylsulfonyl-N-methyl-aminopyridin-2-yl)sulfonylurea, or salts thereof;

b6) alkoxyphenoxysulfonylureas, as described, for example, in EP-A 0 342 569, preferably those of the formula

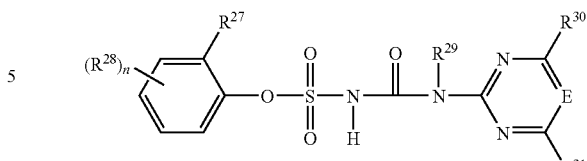

in which

E is CH or N, preferably CH, $R^{27}$ is ethoxy, propoxy or isopropoxy, $R^{28}$ is halogen, $NO_2$, $CF_3$, CN, $(C_1-C_4)$-alkyl, $(C_1-C_4)$-alkoxy, $(C_1-C_4)$-alkylthio or $(C_1-C_3)$-alkoxy-carbonyl, preferably in the 6-position on the phenyl ring, n is 0, 1, 2 or 3, preferably 0 or 1, $R^{29}$ is hydrogen, $(C_1-C_4)$-alkyl or $(C_3-C_4)$-alkenyl, $R^{30}$, $R^{31}$ independently of one another are halogen, $(C_1-C_2)$-alkyl, $(C_1-C_2)$-alkoxy, $(C_1-C_2)$-haloalkyl, $(C_1-C_2)$-haloalkoxy or $(C_1-C_2)$-alkoxy-$(C_1-C_2)$-alkyl, preferably $OCH_3$ or $CH_3$, for example 3-(4,6-dimethoxypyrimidin-2-yl)-1-(2-ethoxyphenoxy)sulfonylurea, or salts thereof;

b7) imidazolylsulfonylureas, for example

MON 37500, sulfosulfuron (see Brighton Crop Prot. Conf. "Weeds", 1995, p. 57), and other related sulfonylurea derivatives and mixtures thereof.

Typical representatives of these active compounds are, inter alia, the compounds listed below: amidosulfuron, azimsulfuron, bensulfuron-methyl, chlorimuron-ethyl, chlorsulfuron, cinosulfuron, cyclosulfamuron, ethametsulfuron-methyl, ethoxysulfuron, flazasulfuron, flupyrsulfuron-methyl-sodium, halosulfuron-methyl, imazosulfuron, metsulfuron-methyl, nicosulfuron, oxasulfuron, primisulfuron-methyl, prosulfuron, pyrazosulfuron-ethyl, rimsulfuron, sulfometuron-methyl, sulfosulfuron, thifensulfuron-methyl, triasulfuron, tribenuron-methyl, triflusulfuron-methyl, iodosulfuron-methyl and its salts, such as the sodium salt (WO 92/13845), mesosulfuron-methyl and its salts, such as the sodium salt (Agrow No. 347, Mar. 3, 2000, page 22 (PJB Publications Ltd. 2000)) and foramsulfuron and its salts such as the sodium salt (Agrow No. 338, Oct. 15, 1999, page 26 (PJB Publications Ltd. 2000)).

The active compounds listed above are known, for example, from The Pesticide Manual, 12th edition (1999), The British Crop Protection Council, or the literature references listed after the individual active compounds.

Preferred combinations of polycarboxylic acid alkyl esters a) and ALS inhibitors b) are those, in which the components a) and b) which have been mentioned as being preferred are combined. Particularly preferred combinations of polycarboxylic acid alkyl esters a) and ALS inhibitors b) are combinations of amidosulfuron with one or more, preferably one, polycarboxylic acid alkyl ester selected from the group consisting of dimethyl oxalate, diethyl oxalate, di-n-propyl oxalate, diisopropyl oxalate, methyl ethyl oxalate, dimethyl malonate, diethyl malonate, di-n-propyl malonate, diisopropyl malonate, methyl ethyl malonate, dimethyl succinate, diethyl succinate, di-n-propyl succinate, diisopropyl succinate, methyl ethyl succinate, dimethyl glutarate, diethyl glutarate, di-n-propyl glutarate, diisopropyl glutarate, methyl ethyl glutarate, dimethyl adipate, diethyl adipate, di-n-propyl adipate, diisopropyl adipate and methyl ethyl adipate, of ethoxysulfuron with one or more, preferably one, polycarboxylic acid alkyl ester selected from the group consisting of dimethyl oxalate, diethyl oxalate, di-n-propyl oxalate, diisopropyl oxalate, methyl ethyl oxalate, dimethyl malonate, diethyl malonate, di-n-propyl malonate, diisopropyl malonate, methyl ethyl malonate, dimethyl succinate, diethyl succinate, di-n-propyl succinate, diisopropyl succinate, methyl ethyl succinate, dimethyl glutarate, diethyl glutarate, di-n-propyl glutarate, diisopropyl glutarate, methyl ethyl glutarate, dimethyl adipate, diethyl adipate, di-n-propyl adipate, diisopropyl adipate and methyl ethyl adipate, of iodosulfuron-methyl and/or its sodium salt with one or more, preferably one, polycarboxylic acid alkyl ester selected from the group consisting of dimethyl oxalate, diethyl oxalate, di-n-propyl oxalate, diisopropyl oxalate, methyl ethyl oxalate, dimethyl malonate, diethyl malonate, di-n-propyl malonate, diisopropyl malonate, methyl ethyl malonate, dimethyl succinate, diethyl succinate, di-n-propyl succinate, diisopropyl succinate, methyl ethyl succinate, dimethyl glutarate, diethyl glutarate, di-n-propyl glutarate, diisopropyl glutarate, methyl ethyl glutarate, dimethyl adipate, diethyl adipate, di-n-propyl adipate, diisopropyl adipate and methyl ethyl adipate, of foramsulfuron and/or its sodium salt with one or more, preferably one, polycarboxylic acid alkyl ester selected from the group consisting of dimethyl oxalate, diethyl oxalate, di-n-propyl oxalate, diisopropyl oxalate, methyl ethyl oxalate, dimethyl malonate, diethyl malonate, di-n-propyl malonate, diisopropyl malonate, methyl ethyl malonate, dimethyl succinate, diethyl succinate, di-n-propyl succinate, diisopropyl succinate, methyl ethyl succinate, dimethyl glutarate, diethyl glutarate, di-n-propyl glutarate, diisopropyl glutarate, methyl ethyl glutarate, dimethyl adipate, diethyl adipate, di-n-propyl adipate, diisopropyl adipate and methyl ethyl adipate, and of mesosulfuron methyl and/or its sodium salt with one or more, preferably one, polycarboxylic acid alkyl ester selected from the group consisting of dimethyl oxalate, diethyl oxalate, di-n-propyl oxalate, diisopropyl oxalate, methyl ethyl oxalate, dimethyl malonate, diethyl malonate, di-n-propyl malonate, diisopropyl malonate, methyl ethyl malonate, dimethyl succinate, diethyl succinate, di-n-propyl succinate, diisopropyl succinate, methyl ethyl succinate, dimethyl glutarate, diethyl glutarate, di-n-propyl glutarate, diisopropyl glutarate, methyl ethyl glutarate, dimethyl adipate, diethyl adipate, di-n-propyl adipate, diisopropyl adipate and methyl ethyl adipate.

In a further preferred embodiment, the liquid formulations according to the invention comprise, as component a), one or more, preferably one, polycarboxylic acid alkyl ester selected from the group consisting of dimethyl oxalate, diethyl oxalate, di-n-propyl oxalate, diisopropyl oxalate, methyl ethyl oxalate, dimethyl malonate, diethyl malonate, di-n-propyl malonate, diisopropyl malonate, methyl ethyl malonate, dimethyl succinate, diethyl succinate, di-n-propyl succinate, diisopropyl succinate, methyl ethyl succinate, dimethyl glutarate, diethyl glutarate, di-n-propyl glutarate, diisopropyl glutarate, methyl ethyl glutarate, dimethyl adipate, diethyl adipate, di-n-propyl adipate, diisopropyl adipate and methyl ethyl adipate, preferably dimethyl adipate, and, as component b), mixtures of two or more sulfonylureas, for example amidosulfuron/iodosulfuron-methyl, amidosulfuron/iodosulfuron-methyl sodium, foramsulfuron/iodosulfuron-methyl, foramsulfuron/iodosulfuron-methyl sodium, foramsulfuron sodium/iodosulfuron-methyl, foramsulfuron sodium/iodosulfuronmethyl sodium, mesosulfuron-methyl/iodosulfuron-methyl, mesosulfuronmethyl/iodosulfuron-methyl sodium, mesosulfuron-methyl sodium/iodosulfuron-methyl and mesosulfuron-methyl sodium/iodosulfuron-methyl sodium. It is also possible for the formulations to comprise safeners, for example mefenpyr-diethyl, isoxadifen-ethyl or cloquintocet-mexyl.

If appropriate, the liquid formulations of the present invention may, in addition to components a) and b) comprise one or more auxiliaries and additives as further components, for example:

(c) surfactants such as dispersants and emulsifiers and/or non-surfactant polymers, (d) organic solvents different from component a), (e) agrochemicals different from ALS inhibitors, for example herbicides, insecticides, fungicides, safeners, growth regulators or fertilizers, (f) customary formulation auxiliaries, such as antifoams, antifreeze, evaporation inhibitors, preservatives, odorants, colorants, stabilizers, dessicants or thickeners, (g) tank mix components, and/or (h) additional water.

Thus, the liquid formulations of the present invention may comprise, as component c), for example one or more surfactants, e.g. ionic, nonionic or betainic surfactants.

These can be of monomeric or polymeric nature (for example graft polymers). Examples of component c) are surfactants based on silicone, such as trisiloxane surfactants, derivatives of polydimethylsiloxanes and/or silicone oils, or sugar-based surfactants, such as Atplus® 309 F (Uniqema). Further examples of component c) are $(C_4-C_{30})$-(poly)alkylene oxide adducts, which may be, for example, branched, linear, saturated or unsaturated, in particular of fatty alcohols and/or fatty acids and/or fatty acid esters. Examples of (poly)alkylene oxide adducts are Soprophor® CY8 (Rhodia), Genapol® X-060, Genapol® X-080, Genapol® X-150, Genapol® X-200, Sapogenat T® 300, Sapogenat T® 500, Genapol® T 200, Genapol T® 800 and Genagen® MEE (methyl ester ethoxylates, Clariant) and other terminally capped surfactants having a methyl, ethyl, n-propyl, isopropyl, n-butyl, tert-butyl, isobutyl, sec-butyl or acetyl group as terminal grouping, for example Genapol® X-060 methyl ether or Genapol® X-150 methyl ether.

Other examples of component c) are components which are insoluble in the continuous phase of the formulation, for example anionic surfactants such as Hostapur® OSB (Clariant), Netzer® IS (Clariant), Galoryl® DT 201 (CFPI), Tamol® (BASF) or Morwet® D 425 (Witco). By incorporating components which are insoluble in the continous phase or else insoluble active compounds into the formulations, dispersions are obtained. Accordingly, the present invention also embraces dispersions.

Possible components c) include sulfosuccinates, for example those of the formula (III)

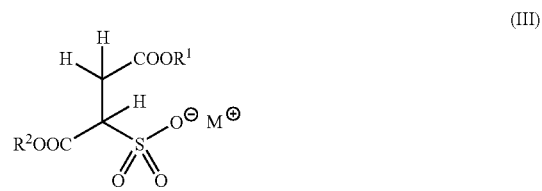

(III)

in which $R^1, R^2$ independently of one another are identical or different and are an unsubstituted or substituted $C_1-C_{30}$-hydrocarbon radical, such as $C_1-C_{3-0}$-alkyl, or a (poly)alkylene oxide adduct, and $M^{\oplus}$ is a cation, for example a metal cation, such as an alkali metal or alkaline earth metal cation, an ammonium cation, such as $NH_4$, alkyl-, alkylaryl- or poly(arylalkyl)phenyl-ammonium cation or (poly)alkylene oxide adducts thereof, or an amino-terminated (poly)alkylene oxide adduct.

For the purpose of this description, (poly)alkylene oxide adducts are reaction products of starting materials which can be alkoxylated, such as alcohols, amines, carboxylic acids, such as fatty acids, hydroxy- or amino-functional carboxylic esters (for example triglycerides based on castor oil) or carboxamides with alkylene oxides, where the (poly)alkylene oxide adducts have at least one alkylene oxide unit but are generally polymeric, i.e. have 2-200, preferably 5-150, alkylene oxide units. Among the alkylene oxide units, preference is given to ethylene oxide, propylene oxide and butylene oxide units, in particular to ethylene oxide units. The (poly) alkylene oxide adducts described can be constructed of identical or different alkylene oxides, for example of propylene oxide and ethylene oxide arranged in blocks or randomly, and, accordingly, the present application also comprises such mixed alkylene oxide adducts.

Possible components c) are furthermore non-surfactant polymers, for example polyvinyl alcohols, polyacrylates, polymalates or polyethylene oxides.

The polymers present as component c) can be inorganic (for example silicates, phosphates) or organic, cationic, anionic or neutral and synthetic or naturally occurring.

Moreover, the liquid formulations according to the invention may also comprise, as component d), various organic solvents different from component a), such as nonpolar solvents, polar protic or aprotic dipolar solvents and mixtures thereof. Examples of organic solvents d) are aliphatic or aromatic hydrocarbons, for example mineral oils, paraffins or toluene, xylenes and naphthalene derivatives, in particular 1-methylnaphthalene, 2-methylnaphthalene, mixtures of $C_6$-$C_{16}$-aromatic compounds, such as the Solvesso® group (ESSO), for example with the types Solvesso® 100 (b.p. 162-177° C.), Solvesso® 150 (b.p. 187-207° C.) and Solvesso® 200 (b.p. 219-282° C.) and $C_6$-$C_{20}$-aliphatic compounds, which may be linear or cyclic, such as the products of the Shellsol® group, types T and K, or BP-n paraffins, halogenated aliphatic or aromatic hydrocarbons, such as methylene chloride or chlorobenzene, esters such as triacetin (acetic acid triglyceride), butyrolactone, propylene carbonate, triethyl citrate and ($C_1$-$C_{22}$)alkyl phthalates, especially ($C_1$-$C_8$)alkyl phthalates, ($C_1$-$C_{1-3}$)alkyl maleates, linear, branched, saturated or unsaturated $C_1$-$C_{20}$-alcohols, such as methanol, ethanol, n- and isopropanol, n-, iso-, sec-, and tert-butanol, tetrahydrofurfuryl alcohol, and also pentanol, hexanol, heptanol ethers, such as diethyl ether, tetrahydrofuran (THF), dioxane, alkylene glycol monoalkyl ethers and dialkyl ethers, such as, for example, propylene glycol monomethyl ether, especially Dowanol® PM (propylene glycol monomethyl ether), propylene glycol monoethyl ether, ethylene glycol monomethyl ether or monoethyl ether, diglyme and tetraglyme, amides, such as dimethylformamide (DMF), dimethylacetamide, dimethylcaprylamide/dimethylcapric amide and N-alkylpyrrolidones, ketones, such as the water-soluble acetone, but also water-imiscible ketones, such as, for example, cyclohexanone or isophorone, nitriles, such as acetonitrile, propionitrile, butyronitrile and benzonitrile, sulfoxides and sulfones, such as dimethyl sulfoxide (DMSO) and sulfolane, and also oils in general, such as mineral oils or vegetable oils, such as corn oil, linseed oil and rapeseed oil.

Organic solvents which are preferred for the purpose of the present invention as components d) are ester oils, such as rapeseed oil methyl ester, and aliphatic or aromatic hydrocarbons, such as Solvesso® types, for example Solvesso® 200 or Solvesso® 150.

The liquid formulations according to the invention may, as component e), comprise agrochemicals which are different from ALS inhibitors. These are, for example, herbicides different from ALS inhibitors, for example from the group of the (het)aryloxyphenoxypropionates, such as diclofop-methyl or quizalofop esters, from the group of the heteroaryloxyphenoxypropionates, such as fenoxaprop-ethyl or clodinafop-propargyl, or from the group of the alkylazines, or else safeners, fertilizers, insecticides, fungicides or acaricides.

Herbicides which are different from ALS inhibitors are, for example, herbicides from the group of the carbamates, thiocarbamates, haloacetanilides, substituted phenoxy-, naphthoxy- and phenoxyphenoxycarboxylic acid derivatives and also heteroaryloxyphenoxyalkanecarboxylic acid derivatives, such as quinolyloxy-, quinoxalyloxy-, pyridyloxy-, benzoxazolyloxy- and benzthiazolyloxyphenoxyalkanecarboxylic esters, cyclohexanedione derivatives, derivatives and also S-(N-aryl-N-alkylcarbamoylmethyl) dithiophosphoric esters. Preference is given here to phenoxyphenoxy- and heteroaryloxyphenoxy herbicides and to herbicides which are used together with ALS inhibitors (acetolactate synthetase inhibitors) for widening the activity spectrum, for example bentazone, cyanazine, atrazine, dicamba, diflufenican or hydroxybenzonitriles such as bromoxynil and ioxynil and other foliar herbicides.

Suitable herbicides which may be present in the formulations according to the invention as component e) are, for example:

A) herbicides of the type of the phenoxyphenoxy- and heteroaryloxyphenoxycarboxylic acid derivatives, such as A1) phenoxyphenoxy- and benzyloxyphenoxycarboxylic acid derivatives, for example methyl 2-(4-(2,4-dichlorophenoxy)phenoxy)propionate (diclofop-methyl), methyl 2-(4-(4-bromo-2-chlorophenoxy)phenoxy)propionate (DE-A 26 01 548), methyl 2-(4-(4-bromo-2-fluorophenoxy)phenoxy)propionate (U.S. Pat. No. 4,808,750), methyl 2-(4-(2-chloro-4-trifluoromethylphenoxy)phenoxy)propionate (DE-A 24 33 067), methyl 2-(4-(2-fluoro-4-trifluoromethylphenoxy)phenoxy)propionate (U.S. Pat. No. 4,808,750), methyl 2-(4-(2,4-dichlorobenzyl)phenoxy)propionate (DE-A 24 17 487), ethyl 4-(4-(4-trifluoromethylphenoxy)phenoxy)pent-2-enoate, methyl 2-(4-(4-trifluoromethylphenoxy)phenoxy)propionate (DE-A 24 33 067);

A2) "monocyclic" heteroaryloxyphenoxyalkanecarboxylic acid derivatives, for example ethyl 2-(4-(3,5-dichloropyridyl-2-oxy)phenoxy)propionate (EP-A 0 002 925), propargyl 2-(4-(3,5-dichloropyridyl-2-oxy)phenoxy)propionate (EP-A 0 003 114), methyl 2-(4-(3-chloro-5-trifluoromethyl-2-pyridyloxy)phenoxy)propionate (EP-A 0 003 890), ethyl 2-(4-(3-chloro-5-trifluoromethyl-2-pyridyloxy)phenoxy)propionate (EP-A 0 003 890), propargyl 2-(4-(5-chloro-3-fluoro-2-pyridyloxy)phenoxy)propionate (EP-A 0 191 736), butyl 2-(4-(5-trifluoromethyl-2-pyridyloxy)phenoxy)propionate (fluazifop-butyl);

A3) "bicyclic" heteroaryloxyphenoxyalkanecarboxylic acid derivatives, for example methyl and ethyl 2-(4-(6-chloro-2-quinoxalyloxy)phenoxy)propionate (quizalofopmethyl and quizalofopethyl), methyl 2-(4-(6-fluoro-2-quinoxalyloxy)phenoxy)propionate (see J. Pest. Sci. Vol. 10, 61

(1985)), 2-isopropylideneaminooxyethyl 2-(4-(6-chloro-2-quinoxalyloxy)phenoxy)propionate (propaquizafop), ethyl 2-(4-(6-chlorobenzoxazol-2-yloxy)phenoxy)propionate (fenoxaprop-ethyl), its D(+) isomer (fenoxaprop-P-ethyl) and ethyl 2-(4-(6-chlorobenzothiazol-2-yloxy)phenoxy)propionate (DE-A 26 40 730), tetrahydro-2-furylmethyl 2-(4-(6-chloroquinoxalyloxy)phenoxy) propionate (EP-A 0 323 727);

B) chloroacetanilides, for example N-methoxymethyl-2,6-diethyl-chloroacetanilide (alachlorine), N-(3-methoxyprop-2-yl)-2-methyl-6-ethylchloroacetanilide (metolachlor), 2,6-dimethyl-N-(3-methyl-1,2,4-oxadiazol-5-ylmethyl)chloroacetanilide, N-(2,6-dimethylphenyl)-N-(1-pyrazolylmethyl)chloroacetamide (metazachlor);

C) thiocarbamates, for example S-ethyl N,N-dipropylthiocarbamate (EPTC), S-ethyl N,N-diisobutylthiocarbamate (butylate);

D) cyclohexanedione oximes, for example methyl 3-(1-allyloxyiminobutyl)-4-hydroxy-6,6-dimethyl-2-oxocyclohex-3-enecarboxylate (alloxydim), 2-(1-ethoxyiminobutyl)-5-(2-ethylthiopropyl)-3-hydroxycyclohex-2-ene-1-one (sethoxydim), 2-(1-ethoxyiminobutyl)-5-(2-phenylthiopropyl)-3-hydroxycyclohex-2-ene-1-one (cloproxydim), 2-(1-(3-chloroallyloxy)iminobutyl)-5-(2-ethylthiopropyl)-3-hydroxycyclohex-2-ene-1-one, 2-(1-(3-chloroallyloxy)iminopropyl)-5-(2-ethylthiopropyl)-3-hydroxycyclohex-2-ene-1-one (clethodim), 2-(1-ethoxyiminobutyl)-3-hydroxy-5-(thian-3-yl)cyclohex-2-enone (cycloxydim), 2-(1-ethoxyiminopropyl)-5-(2,4,6-trimethylphenyl)-3-hydroxycyclohex-2-ene-1-one (tralkoxydim);

E) benzoylcyclohexanediones, for example 2-(2-chloro-4-methylsulfonylbenzoyl)cyclohexane-1,3-dione (SC-0051, EP-A 0 137 963), 2-(2-nitrobenzoyl)-4,4-dimethylcyclohexane-1,3-dione (EP-A 0 274 634), 2-(2-nitro-3-methylsulfonylbenzoyl)-4,4-dimethylcyclohexane-1,3-dione (WO 91/13548);

F) S-(N-aryl-N-alkylcarbamoylmethyl) dithiophosphonates, such as S-[N-(4-chlorophenyl)-N-isopropylcarbamoylmethyl]O,O-dimethyl dithiophosphate (anilophos);

G) alkylazines, such as, for example, described in WO-A 97/08156, WO-A-97/31904, DE-A-19826670, WO-A-98/15536, WO-A-8/15537, WO-A-98/15538, WO-A-98/15539 and also DE-A-1 9828519, WO-A-98/34925, WO-A-98/42684, WO-A-99/188100, WO-A-99/19309, WO-A-99/37627 and WO-A-99/65882, preferably those of the formula (E)

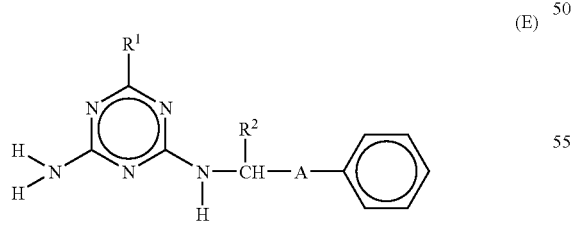

(E)

in which
$R^1$ is $(C_1-C_4)$-alkyl or $(C_1-C_4)$-haloalkyl;
$R^2$ is $(C_1-C_4)$-alkyl, $(C_3-C_6)$-cycloalkyl or $(C_3-C_6)$-cycloalkyl-$(C_1-C_4)$-alkyl and
A is —CH$_2$—, —CH$_2$—CH$_2$—, —CH$_2$—CH$_2$—CH$_2$—, —O—, —CH$_2$—CH$_2$—O—, —CH$_2$—CH$_2$—CH$_2$—O—, particularly preferably those of the formulae E1-E7

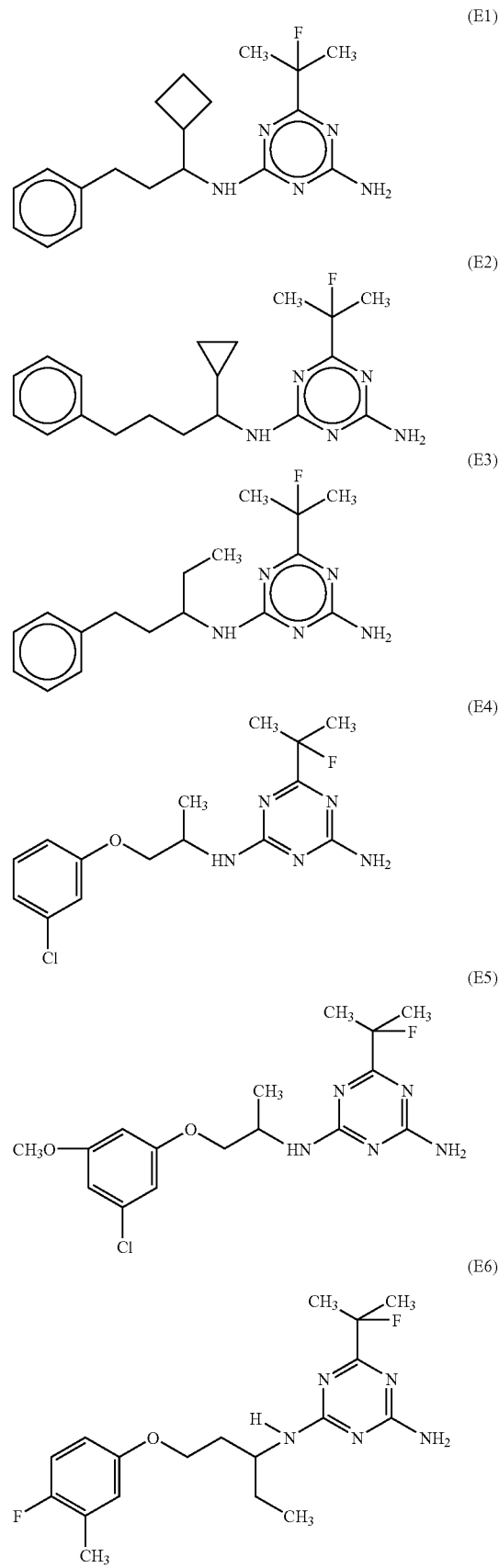

-continued

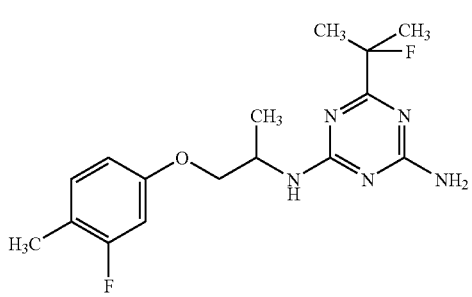
(E7)

The herbicides of groups A to G are known, for example, from the above-mentioned publications and from "The Pesticide Manual", The British Crop Protection Council, 12th Edition, 2000 (abbreviated to PM), "Agricultural Chemicals Book II—Herbicides", by W. T. Thompson, Thompson Publications, Fresno Calif., USA 1990 and "Farm Chemicals Handbook '90", Meister Publishing Company, Willoughby Ohio, USA, 1990.

The following groups of compounds may, for example, be present as safeners in the formulations according to the invention, as component e):

a) compounds of the type of dichlorophenylpyrazoline-3-carboxylic acid (S1), preferably compounds such as ethyl 1-(2,4-dichlorophenyl)-5-(ethoxycarbonyl)-5-methyl-2-pyrazoline-3-carboxylate (S1-1), and related compounds (mefenpyr di($C_1$-$C_{1-5}$-alkyl) esters, such as mefenpyr-diethyl), as described in WO 91/07874 and PM pp. 594-595, b) derivatives of dichlorophenylpyrazole carboxylic acid, preferably compounds such as ethyl 1-(2,4-dichlorophenyl)-5-methylpyrazole-3-carboxylate (S1-2), ethyl 1-(2,4-dichlorophenyl)-5-isopropylpyrazole-3-carboxylate (S1-3), ethyl 1-(2,4-dichlorophenyl)-5-(1,1-dimethylethyl) pyrazole-3-carboxylate (S1-4), ethyl 1-(2,4-dichlorophenyl)-5-phenylpyrazole-3-carboxylate (S1-5) and related compounds as described in EP-A-333 131 and EP-A-269 806, c) compounds of the type of the triazolecarboxylic acids (S1), preferably compounds such as fenchlorazole, i.e. ethyl 1-(2,4-dichlorophenyl)-5-trichloro-methyl-(1H)-1,2,4-triazole-3-carboxylate (S1-6) and related compounds (see EP-A-174 562 and EP-A-346 620);

d) compounds of the type of the 5-benzyl- or 5-phenyl-2-isoxazoline-3-carboxylic acid, or the 5,5-diphenyl-2-isoxazoline-3-carboxylic acid, preferably compounds such as ethyl 5-(2,4-dichlorobenzyl)-2-isoxazoline-3-carboxylate (S1-7) or ethyl 5-phenyl-2-isoxazoline-3-carboxylate (S1-8) and related compounds, as described in WO 91/08202, or ethyl 5,5-diphenyl-2-isoxazolinecarboxylate (S1-9, isoxadifen-ethyl) or n-propyl ester (S1-10) or ethyl 5-(4-fluorophenyl)-5-phenyl-2-isoxazoline-3-carboxylate (S1-11), as described in the German patent application (WO-A-95/07897), e) compounds of the type of the 8-quinolineoxyacetic acid (S2), preferably 1-methylhex-1-yl (5-chloro-8-quinolineoxy)acetate (S2-1, cloquintocet-mexyl, e.g. PM (pp. 195-196)), 1,3-dimethylbut-1-yl (5-chloro-8-quinolineoxy)acetate (S2-2), 4-allyloxybutyl (5-chloro-8-quinolineoxy) acetate (S2-3), 1-allyloxyprop-2-yl (5-chloro-8-quinolineoxy)acetate (S2-4), ethyl (5-chloro-8-quinolineoxy)acetate (S2-5), methyl (5-chloro-8-quinolineoxy)acetate (S2-6), allyl (5-chloro-8-quinolineoxy)acetate (S2-7), 2-(2-propylideneiminoxy)-1-ethyl (5-chloro-8-quinolineoxy)acetate (S2-8), 2-oxoprop-1-yl (5-chloro-8-quinolineoxy)acetate (S2-9) and related compounds, as described in EP-A-86 750, EP-A-94 349 and EP-A-191 736 or EP-A-0 492 366, f) compounds of the type of the (5-chloro-8-quinolineoxy) malonic acid, preferably compounds such as diethyl (5-chloro-8-quinolineoxy)malonate, diallyl (5-chloro-8-quinolineoxy)malonate, methyl ethyl (5-chloro-8-quinolineoxy)malonate and related compounds, as described in EP-A-0 582 198, g) active compounds of the type of the phenoxyacetic or -propionic acid derivatives or the aromatic carboxylic acids, such as, for example,
2,4-dichlorophenoxyacetic acid (esters) (2,4-D),
4-chloro-2-methylphenoxypropionic esters (mecoprop), MCPA or 3,6-dichloro-2-methoxybenzoic acid (esters) (dicamba), h) active compounds of the type of the pyrimidines, which are used as soil-acting safeners in rice, such as, for example,
"fenclorim" (PM, pp. 386-387) (=4,6-dichloro-2-phenylpyrimidine), which is known as safener for pretilachlor in sown rice, i) active compounds of the type of the dichloroacetamides, which are frequently used as pre-emergent safeners (soil-acting safeners), such as, for example, "dichlormid" (PM, pp. 270-271) (=N,N-diallyl-2,2-dichloroacetamide),
"R-29148" (=3-dichloroacetyl-2,2,5-trimethyl-1,3-oxazolidone from Stauffer),
"benoxacor" (PM, pp. 74-75) (=4-dichloroacetyl-3,4-dihydro-3-methyl-2H-1,4-benzoxazine),
"PPG-1292" (=N-allyl-N-[(1,3-dioxolan-2-yl)methyl] dichloroacetamide from PPG Industries),
"DK-24" (=N-allyl-N-[(allylaminocarbonyl)methyl] dichloroacetamide from Sagro-Chem),
"AD-67" or "MON 4660" (=3-dichloroacetyl-1-oxa-3-aza-spiro[4,5]decane from Nitrokemia or Monsanto),
"diclonon" or "BAS145138" or "LAB145138" (=3-dichloroacetyl-2,5,5-trimethyl-1,3-diazabicyclo[4.3.0] nonane from BASF) and
"furilazol" or "MON 13900" (see PM, 482-483) (=(RS)-3-dichloroacetyl-5-(2-furyl)-2,2-dimethyloxazolidone), j) active compounds of the type of the dichloroacetone derivatives, such as, for example,
"MG 191" (CAS-Reg. No. 96420-72-3) (=2-dichloromethyl-2-methyl-1,3-dioxolane from Nitrokemia), which is known as safener for corn, k) active compounds of the type of the oxyimino compounds, which are known as seed dressings, such as, for example,
"oxabetrinil" (PM, p. 689) (=(Z)-1,3-dioxolan-2-ylmethoxy-imino(phenyl)acetonitrile), which is known as seed dressing safener against metolachlor damage,
"fluxofenim" (PM, pp. 467-468) (=1-(4-chlorophenyl)-2, 2,2-trifluoro-1-ethanone O-(1,3-dioxolan-2-ylmethyl) oxime), which is known as seed dressing safener against metolachlor damage, and
"cyometrinil" or "-CGA43089" (PM, p. 983) (=(Z)-cyanomethoxyimino(phenyl)acetonitrile), which is known as seed dressing safener against metolachlor damage, l) active compounds of the type of the thiazolecarboxylic esters, which are known as seed dressings, such as, for example,
"flurazol" (PM, pp. 450-451) (=benzyl 2-chloro4-trifluoromethyl-1,3-thiazole-5-carboxylate), which is known as seed dressing safener against alachlor and metolachlor damage, m) active compounds of the type of the naphthalenedicarboxylic acid derivatives, which are known as seed dressings, such as, for example, "naphthalic anhydride" (PM, pp. 1009-1010) (=1,8-naphthalenedicarboxylic anhydride), which is known as seed dressing safener for corn against thiocarbamate herbicide damage, n) active compounds of the type of the chromanacetic acid derivatives, such as, for example, "CL 304415" (CAS-Reg. No. 31541-57-8) (=2-84-carboxychroman-4-yl)acetic acid from American Cyanamid), which is known as safener for corn against imidazolinone damage, o) active compounds which, in addition to a herbicidal action against harmful plants, also have safener action on crop plants such as rice, such as, for example, "dimepiperate" or "MY-93" (PM, pp. 302-303) (=S-1-methyl-1-phenylethyl piperidine-1-thiocarboxylate), which is known as safener for rice against damage by the herbicide molinate, "daimuron" or "SK 23" (PM, p. 247) (=1-(1-methyl-1-phenylethyl)-3-p-tolylurea), which is known as safener for rice against damage by the herbicide imazosulfuron, "cumyluron"="JC-940" (=3-(2-chlorophenylmethyl)-1-(1-methyl-1-phenylethyl)urea, see JP-A-60087254), which is known as safener for rice against damage by some herbicides, "methoxyphenon" or "NK 049" (=3,3'-dimethyl-4-methoxybenzophenone), which is known as safener for rice against damage by some herbicides, "CSB" (=1-bromo-4-(chloromethylsulfonyl)benzene) (CAS-Reg. No. 54091-06-4 from Kumiai).

Preferred safeners are mefenpyr-diethyl, isoxadifen-ethyl and cloquintocet-mexyl.

In the liquid formulations according to the invention, customary formulation auxiliaries, such as antifoams, antifreeze agents, evaporation inhibitors, preservatives, odorants, colorants, stabilizers, dessicants or thickeners may be present as component f). Preferred formulation auxiliaries are antifreeze agents and evaporation inhibitors such as glycerol, for example in an amount of from 2 to 10% by weight, and preservatives, for example Mergal® K9N (Riedel) or Cobate® C.

The formulations according to the invention may also, as component g), comprise tank mix components. Examples of these are tank mix adjuvants, such as Telmion® (Hoechst) or vegetable oils such as Actirob B® (Novance) or Hasten® (Victorian Chemicals), inorganic compounds such as fertilizers, for example ammonium sulfate, ammonium nitrate, ammonium hydrogen sulfate,ureas or hydrotropics.

The formulations according to the invention may also comprise, as component h), additional water.

The liquid formulations according to the invention can be present, for example, in the form of solutions, emulsion concentrates or dispersions, such as emulsions or suspensions. Here, preferably at least one active compound from the group of the ALS inhibitors, preferably at least one sulfonylurea, is present in dissolved form. In a further preferred embodiment, all active compound ingredients are dissolved.

It is possible to convert the solutions according to the invention comprising components a) and b) and, if appropriate, components c), d), e), f) and g) by addition of water into microemulsions and/or macroemulsions or solutions. Thus, in addition to solutions in polycarboxylic acid alkyl esters a) and/or in organic solvents, the present invention also embraces water-containing formulations such as microemulsions and macroemulsions (for example EW and EO formulations).

By incorporating active compounds or components which are insoluble in the continuous phase into the formulations, dispersions are obtained. Accordingly, the present invention also embraces such dispersions. On dilution with water, the formulations according to the invention give dispersions or else water-containing solutions, which are likewise embraced by the present invention.

The content of active compound in the formulations according to the invention may be generally between 0.001% by weight and 60% by weight, higher loads being possible in individual cases, in particular when a plurality of active compounds are used. Since ALS inhibitors are highly effective active compounds, the preferred application rates are usually between 1 and 1000 g, preferably 500 g, with preference between 1 and 100 g, of active substance/hectare. In general, the content of polycarboxylic acid derivatives according to the invention is 0.01-99.9%, preferably 0.1-99%; however, this may be higher or lower in individual cases.

Preferred weight ratios of the components a) and b) in the liquid formulations according to the invention, in particular in emulsion concentrates, are 0.1:1-1000:1, preferably 1:1 to 500:1, in particular 1:1 to 200:1. Particular preference is given to an excess by weight of component a) compared to component b), for example about 2:1, 3:1, 5:1, 6:1, 7:1, 10:1, 50:1, 100:1, 200:1, 300:1, 400:1 and 500:1.

The auxiliaries and additives which can be used for preparing the formulations according to the invention, such as, for example, surfactants and solvents, are known in principle and are described, for example, in: McCutcheon's "Detergents and Emulsifiers Annual", MC Publ. Corp., Ridgewood N.J.; Sisley and Wood, "Encyclopedia of Surface Active Agents", Chem. Publ. Co. Inc., N.Y. 1964; Schönfeldt, "Grenzflächenaktive Äthylenoxidaddukte" [Surface-Active Ethylene Oxide Adducts], Wiss. Verlagsgesellschaft, Stuttgart 1976; Winnacker-Küchler, "Chemische Technologie" [Chemical Technology], volume 7, C. Hauser-Verlag, Munich, 4th edition 1986.

The liquid formulations according to the invention can be prepared by customary known processes, i.e., for example, by mixing the different components with the aid of stirrers, shakers or (static) mixers. If appropriate, brief heating may be advantageous. In the case of salt-like ALS inhibitors, this simple process makes it possible to prepare the corresponding ALS inhibitor salts in situ by using, for example, nonionic surfactants, preferably those in which no neutralization has been carried out.

Thus, the present invention also embraces the processes described for preparing the liquid formulations according to the invention. These processes are distinguished in particular by production-related advantages.

In a preferred embodiment, the ALS inhibitors used, such as sulfonylureas, are inhibitors with counterions having phase-transfer properties. Such counterions are, for example, organic counterions, such as organic ammonium, sulfonium or phosphonium ions. Such counterions can be incorporated in a particularly simple manner into the formulations if they are present in admixture with additional, for example nonionic, formulation components. Accordingly, the invention also embraces the incorporation of the counterions into the formulations.

The liquid formulations according to the invention preferably comprise (a) from 0.01 to 99.9% by weight, preferably from 0.1 to 60% by weight, of polycarboxylic acid alkyl esters, (b) from 0.001 to 50% by weight, preferably from 0.1 to 15% by weight, of herbicidally active compounds from the group of the ALS inhibitors, preferably from the group of the sulfonylureas and/or salts thereof,
(c) from 0 to 60% by weight, preferably from 0.1 to 50% by weight, of surfactants and/or non-surfactant polymers,
(d) from 0 to 90% by weight, preferably from 1 to 30% by weight, of organic solvents different from component a),
(e) from 0 to 50% by weight, preferably from 0 to 30% by weight, of agrochemicals different from ALS inhibitors,
(f) from 0 to 20% by weight, preferably from 0 to 10% by weight, of customary formulation auxiliaries, and
(h) from 0 to 50% by weight, preferably from 0 to 10% by weight, of additional water.

Particularly preferred liquid formulations comprise:
a) 0.01-99% by weight of dialkyl dicarboxylates, for example of the structure:

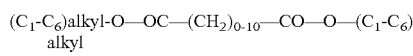

$(C_1-C_6)$alkyl-O—OC—$(CH_2)_{0-10}$—CO—O—$(C_1-C_6)$alkyl b) 0.001-30% by weight of sulfonylureas and/or salts thereof,
c1) optionally 0.5-40% by weight of nonionic surfactants, for example those of the formula

$R\text{-}(EO)_x(PO)_y(EO)_z\text{-}R'$ in which
R is H or a $C_1$-$C_{30}$-hydrocarbonoxy radical, such as di- or tristyrylphenol, mono-, di- or tri-$(C_1$-$C_{10})$alkyl-aryloxy or $(C_1$-$C_{20})$alkyl-(poly)alkenyloxy, preferably $(C_8$-$C_{18})$-alkyloxy or mono-, di- or tri-$(C_1$-$C_{10})$alkylphenyloxy and
R' is H, COH, CO—$(C_1$-$C_6)$alkyl, CO$(C_1$-$C_6)$alkoxy or $(C_1$-$C_6)$alkyl, and
x, y and z are integers from 0 to 200, where $4 \leq x+y+z \leq 200$, preferably $6 \leq x+y+z \leq 100$; particularly preferably x is an integer from 6 to 200, preferably from 8 to 100, and y=z=0, and
c2) optionally 0.5-60% by weight of sulfosuccinates of the formula (IIIa):

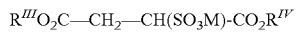

$R^{III}O_2C$—$CH_2$—$CH(SO_3M)$-$CO_2R^{IV}$ (IIIa)

in which
$R^{III}$ and $R^{IV}$ are identical or different $(C_1$-$C_{10})$alkyl, such as 2-ethylhexyl, and
M is a metal cation, for example an alkali metal ion such as Na or K.

These particularly preferred combinations, too, can be formulations in their own right or else form the basis for a finished formulation.

By using the formulations according to the invention, it is possible to obtain storage-stable solutions of ALS inhibitors such as sulfonylureas and/or salts thereof, and also liquid formulations in which at least one sulfonylurea and/or its salt is/are dissolved.

If a sulfonylurea and/or a salt derived therefrom is/are dissolved in component a), it is possible to obtain corresponding liquid formulations by adding surfactants and, if appropriate, further auxiliaries.

The liquid formulations according to the invention can be used, for example, for controlling undesirable vegetation, for example, in crops of plants. To this end, an effective amount of the formulation according to the invention is, if required after dilution with water, applied to the seeds, plants, parts of plants or the area to be treated, for example the area under cultivation.

The formulations according to the invention are formulations which are physically and chemically stable and which, on dilution with water, give spray liquors having favorable physical performance characteristics. In addition, the formulations according to the invention have favorable biological properties and can be used widely, for example for controlling undesirable vegetation.

EXAMPLES

Example 1

1.1 g of iodosulfuron-methyl sodium are added to 98.9 g of dimethyl adipate, and the mixture is stirred until the entire active compound is dissolved. At 40° C., the formulation was storage-stable for more than 2 months.

Example 2

1.05 g of mesosulfuron-methyl are added to 98.95 g of dimethyl adipate, and the mixture is stirred until the entire active compound is dissolved. At 40° C., the formulation was storage-stable for more than 2 months.

Example 3

With stirring, 1.05 g of iodosulfuron-methyl sodium are dissolved in 88.95 g of dimethyl adipate. Once the iodosulfuron-methyl has dissolved, 10 g of Genapol® X-060 methyl ether are added. The mixture is stirred until a clear formulation is obtained. At 40° C., the formulation was storage-stable for more than 2 months.

Example 4

5.38 g of iodosulfuron-methyl sodium, 10 g of Hostapur® SAS 93 G and 84.62 g of dimethyl adipate are homogenized using an Ultraturax. Glass beads are then added to the mixture, which is ground in a bead mill until a homogeneous dispersion is obtained. At 40° C., the formulation was storage-stable for more than 2 months.

Example 5

1.54 g of iodosulfuron-methyl sodium, 4.46 g of mefenpyr-diethyl and 8.02 g of 2-(1-cyclobutyl-4-phenylpropyl)amino-4-amino-6-(1-fluoro-1-methylethyl)-1,3,5-triazine (E1) are added to 58.46 g of dimethyl adipate, 15.00 g of Triton® GR-7ME and 3.0 g of Edenor® MESU. The mixture is stirred until the entire active compound has dissolved. 9.52 g of Genapol® X-060 methyl ether are then added. The mixture is stirred until a clear formulation is obtained. At 40° C., the formulation was storage-stable for more than 2 months.

The invention claimed is:
1. A liquid formulation, comprising
a) one or more compounds from the group of the alkyl esters of polycarboxylic acids of the formula (I)

$R^\gamma$—O—OC—$(CR^\alpha R^\beta)_x$—CO—O—$R^\delta$ (I)

in which
$R^\alpha$ and $R^\beta$ are identical or different and are H, an unsubstituted or substituted $C_1$-$C_{20}$ hydrocarbon radical, or a group $(CR'R'')_y$—CO—OR''', in which R' and R'' are identical or different and are H or an unsubstituted or substituted $C_1$-$C_{20}$-hydrocarbon radical, y is an integer from 0 to 10 and R''' is an unsubstituted or substituted $C_1$-$C_{20}$-hydrocarbon radical, $R^\gamma$ and $R^\delta$ are identical or different and are an unsubstituted or substituted $C_1$-$C_{20}$ hydrocarbon radical, and x is an integer from 0 to 20; and b) one or more agrochemically active compounds selected from the group consisting of iodosulfuron-methyl and salts thereof, at least one being present in dissolved form.

2. The liquid formulation as claimed in claim 1, which comprises, as component b), said one or more agrochemically active compounds selected from the group consisting of iodosulfuron-methyl, and salts thereof, at least one being present in dissolved form in combination with one or more agrochemicals which are not ALS inhibitors.

3. The liquid formulation as claimed in claim 1, further comprising
one or more additional components selected from the group consisting of
(c) surfactants and/or non-surfactant polymers,
(d) organic solvents different from component a),
(e) agrochemicals different from ALS inhibitors,
(f) customary formulation auxiliaries,
(g) tank mix components, and
(h) water.

4. The liquid formulation as claimed in claim 1, comprising
(a) from 0.1 to 80% by weight of said one or more compounds selected from the group consisting of the alkyl esters of polycarboxylic acids of the formula (I),
(b) from 0,001 to 50% by weight of said one or more agrochemically active compounds selected from the group consisting of iodosulfuron-methyl and salts thereof, at least one being present in dissolved form,
(c) from 0 to 60% by weight of surfactants and/or non-surfactant polymers,
(d) from 0 to 90% by weight of organic solvents different from component a),
(e) from 0 to 50% by weight of agrochemicals different from ALS inhibitors,
(f) from 0 to 20% by weight of customary formulation auxiliaries and
(g) from 0 to 50% by weight of water.

5. The liquid formulation as claimed in claim 1, comprising
(a) from 10 to 60% by weight of said one or more compounds selected from the group consisting of the alkyl esters of polycarboxylic acids of the formula (I),
(b) from 1 to 15% by weight of said one or more agrochemically active compounds selected from the group consisting of iodosulfuron-methyl and salts thereof, at least one being present in dissolved form,
(c) from 0 to 50% by weight of surfactants and/or non-surfactant polymers,
(d) from 0 to 30% by weight of organic solvents different from component a),
(e) from 0 to 50% by weight of agrochemicals different from ALS inhibitors and
(f) from 0 to 10% by weight of customary formulation auxiliaries.

6. The liquid formulation as claimed in claim 1 in the form of a solution, a dispersion or an emulsion concentrate.

7. The liquid formulation of claim 1, wherein R' and R" are identical or different and are H or an unsubstituted or substituted $C_1$-$C_{10}$-alkyl radical.

8. The liquid formulation of claim 1, wherein R'" is an unsubstituted or substituted $C_1$-$C_{10}$ alkyl radical.

9. The liquid formulation of claim 1, wherein $R^\gamma$ and $R^\delta$ are identical or different and are an unsubstituted or substituted $C_1$-$C_{10}$ alkyl radical.

* * * * *